(12) United States Patent
Hinchliffe et al.

(10) Patent No.: US 6,217,546 B1
(45) Date of Patent: *Apr. 17, 2001

(54) CATHETER SYSTEM

(75) Inventors: Peter W. J. Hinchliffe, New Haven, CT (US); Thomas J. Dugan, Groton, MA (US)

(73) Assignee: United States Surgical Corporation, Norwalk, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/858,666

(22) Filed: May 19, 1997

(51) Int. Cl.$^7$ .................................................. A61M 29/00
(52) U.S. Cl. ...................... 604/96.01; 604/523; 604/532; 604/6.11; 604/508
(58) Field of Search ............................ 604/28 H, 4, 280, 604/96–102, 104, 523, 532, 533, 534, 500, 131, 132, 133, 4.01, 6.11, 506, 508; 606/192, 194; 600/18

(56) References Cited

U.S. PATENT DOCUMENTS

| 4,173,981 | 11/1979 | Mortensen . |
| 4,531,936 | 7/1985 | Gordon . |
| 4,592,340 | 6/1986 | Boyles . |
| 4,909,258 | 3/1990 | Kuntz et al. . |
| 4,927,412 | 5/1990 | Menasche . |

(List continued on next page.)

FOREIGN PATENT DOCUMENTS

| 3728371 | 8/1987 | (DE) . |
| 0150960 | 8/1985 | (EP) . |
| 0218275 | 4/1987 | (EP) . |
| 0280225 | 8/1988 | (EP) . |
| 0286756 | 10/1988 | (EP) . |

(List continued on next page.)

OTHER PUBLICATIONS

Wareing et al., "Management of the Severly Atherosclerotic Ascending Aorta During Cardiac Operations", The Journal of Thoracic and Cardiovascular Surgery, vol. 103, No. 3, Mar. 1992, pp. 453–462.

Milgaiter et al., "The Inferior Epigastric Arteries as Coronary Bypass Conduits", The Journal of Thoracic Cardiovascular Surgery, vol. 103, No. 3, Mar. 1992, pp. 463–465.

Blauth et al., "Atheroembolism from the Ascending Aorta", Journal of Thoracic and the Cardiovascular Surgery, vol. 103, No. 6, Jun. 1992, pp. 1104–1111.

Underwood et al., "Operative Management of the Calcified Aorta: A Practical Method of Aortic Occlusion", The Journal of Thoracic and Cardiovascular Surgery, vol. 105, No. 2, pp. 377–378.

*Primary Examiner*—John D. Yasko

(57) ABSTRACT

The present application provides an arterial cannula system for transporting blood from an extracorporeal pump to a patient's femoral artery and aorta comprising first and second cannula portions. The first cannula portion has a proximal portion, a distal portion, and an intermediate portion and is configured for insertion through the femoral artery. It includes a first lumen extending from the proximal portion to the distal portion to deliver cardioplegic fluid, a second lumen communicating with an expandable occluding member at the distal end portion to inflate the occluding member to occlude blood flow, and a third lumen extending from the proximal portion to the intermediate portion to transport blood from the extracorporeal pump to the femoral artery. The second cannula portion is configured for insertion into the subclavian artery so that an opening in the distal portion is in communication with the aorta. A lumen extending through the second cannula portion is in communication with the opening to transport blood from the extracorporeal pump to the aorta.

29 Claims, 8 Drawing Sheets

U.S. PATENT DOCUMENTS

| | | |
|---|---|---|
| 4,943,277 | 7/1990 | Bolling . |
| 4,995,865 | 2/1991 | Gahara et al. . |
| 5,011,469 | 4/1991 | Buckberg et al. . |
| 5,021,045 | 6/1991 | Buckberg et al. . |
| 5,024,668 | 6/1991 | Peters et al. . |
| 5,090,960 | 2/1992 | Don Michael . |
| 5,122,115 | 6/1992 | Marks . |
| 5,160,321 | 11/1992 | Sahota . |
| 5,163,905 | 11/1992 | Don Michael . |
| 5,171,218 | 12/1992 | Fonger et al. . |
| 5,190,528 | 3/1993 | Fonger et al. . |
| 5,197,951 | 3/1993 | Mahurkar . |
| 5,197,952 | 3/1993 | Marcadis et al. . |
| 5,207,648 | 5/1993 | Gross . |
| 5,221,256 | 6/1993 | Mahurkar . |
| 5,295,958 | 3/1994 | Shturman . |
| 5,308,319 | 5/1994 | Ide et al. . |
| 5,308,320 | 5/1994 | Safar et al. . |
| 5,312,344 | 5/1994 | Grinfeld et al. . |
| 5,330,451 | 7/1994 | Gabbay . |
| 5,334,142 | 8/1994 | Paradis . |
| 5,354,288 | 10/1994 | Cosgrove et al. . |
| 5,370,617 | 12/1994 | Sahota . |
| 5,383,854 | 1/1995 | Safar et al. . |
| 5,395,316 | 3/1995 | Martin . |
| 5,423,745 | 6/1995 | Todd et al. . |
| 5,433,700 * | 7/1995 | Peters ................................ 604/96 |
| 5,437,637 | 8/1995 | Lieber et al. . |
| 5,451,206 | 9/1995 | Young . |
| 5,452,733 | 9/1995 | Sterman et al. . |
| 5,458,574 | 10/1995 | Machold et al. . |
| 5,478,309 | 12/1995 | Sweezer et al. . |
| 5,486,159 | 1/1996 | Mahurkar . |
| 5,558,644 | 9/1996 | Boyd et al. . |
| 5,573,508 | 11/1996 | Thornton . |
| 5,584,803 | 12/1996 | Stevens et al. . |
| 5,662,620 | 9/1997 | Lieber et al. . |
| 5,755,687 | 5/1998 | Donlon . |
| 5,765,568 | 6/1998 | Sweezer, Jr. et al. . |
| 5,766,151 | 6/1998 | Valley et al. . |
| 5,792,094 | 8/1998 | Stevens . |
| 5,795,325 | 8/1998 | Valley et al. . |

FOREIGN PATENT DOCUMENTS

| | | |
|---|---|---|
| 0301854 | 2/1989 | (EP) . |
| 0357338 | 3/1990 | (EP) . |
| 0604803 | 7/1994 | (EP) . |
| 2194735 | 3/1988 | (GB) . |
| 5337175 | 12/1993 | (JP) . |
| 7707741 | 7/1977 | (NL) . |
| 8702894 | 5/1987 | (WO) . |
| 9001972 | 3/1990 | (WO) . |
| 9206733 | 4/1992 | (WO) . |
| 9217118 | 10/1992 | (WO) . |
| 9418881 | 9/1994 | (WO) . |
| 9508364 | 3/1995 | (WO) . |
| 9510218 | 4/1995 | (WO) . |
| 9515192 | 6/1995 | (WO) . |
| 9515715 | 6/1995 | (WO) . |
| 9516476 | 6/1995 | (WO) . |
| 9524940 | 9/1995 | (WO) . |
| WO 96/17644 | 11/1995 | (WO) . |
| 9532745 | 12/1995 | (WO) . |
| 9621489 | 7/1996 | (WO) . |

* cited by examiner

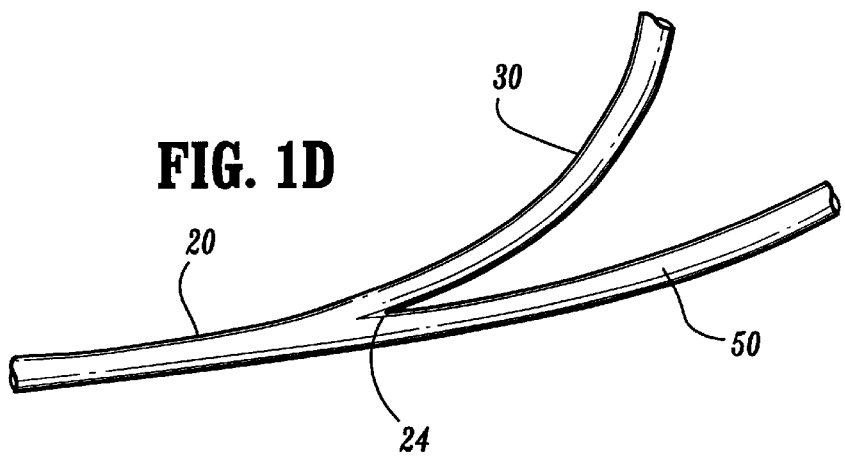
FIG. 1D
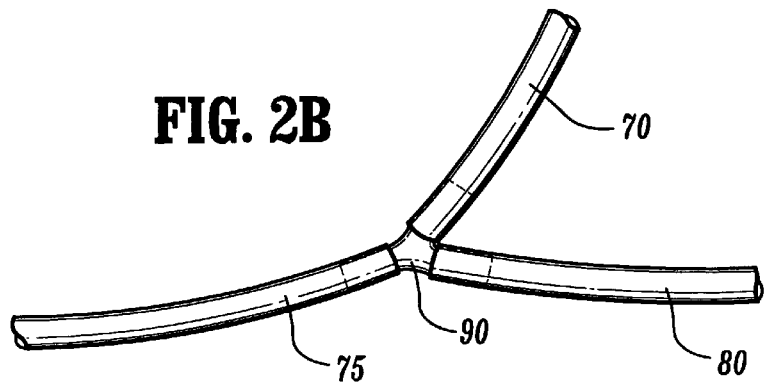
FIG. 2B
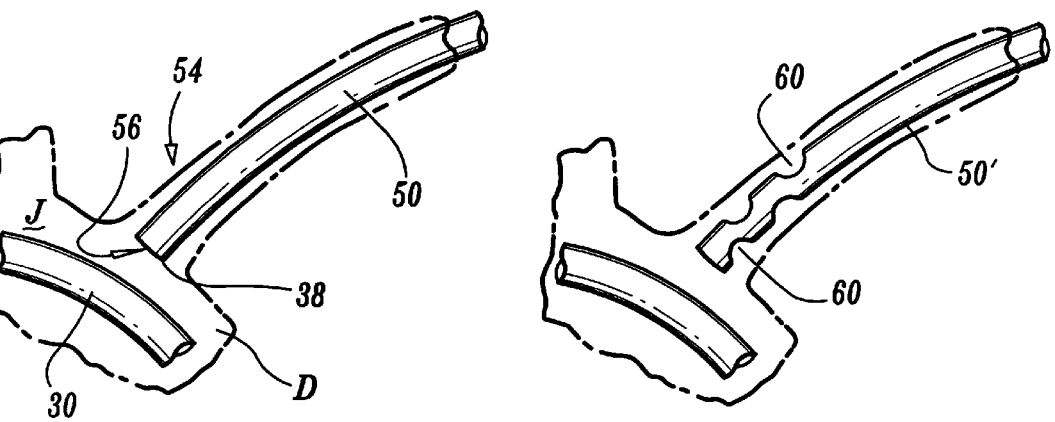
FIG. 3  FIG. 3A

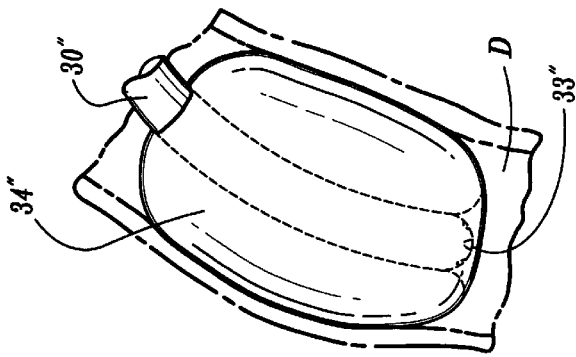
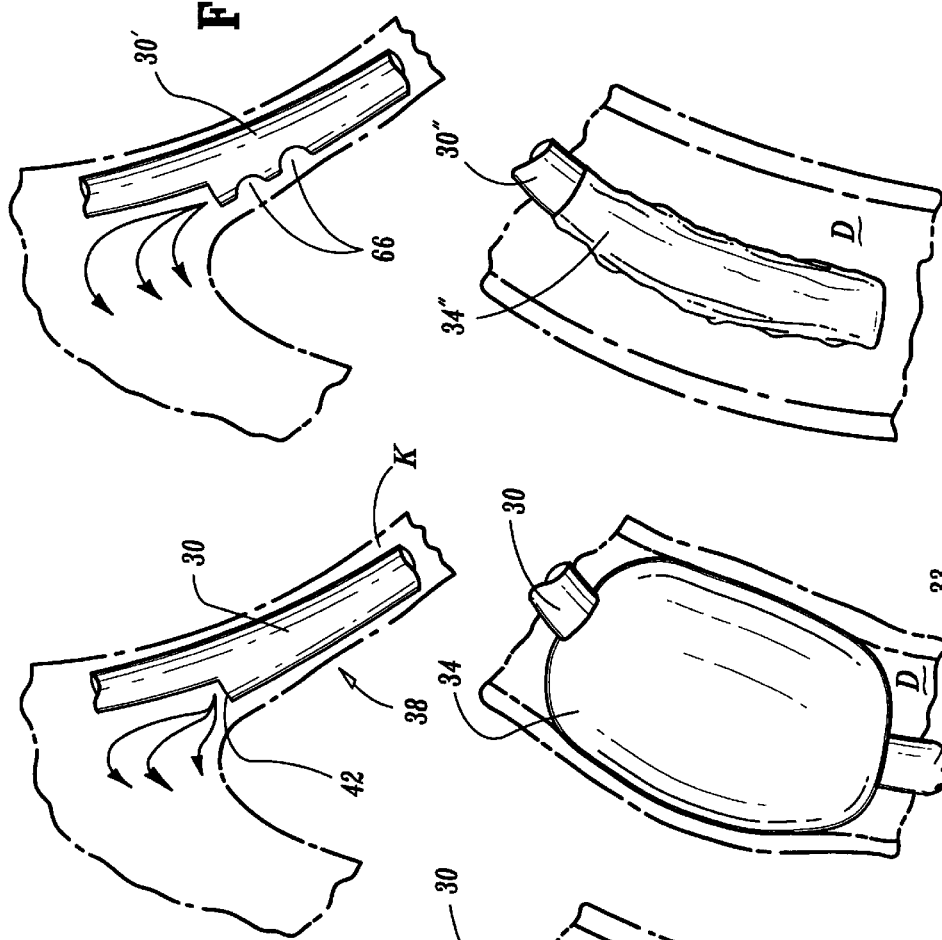
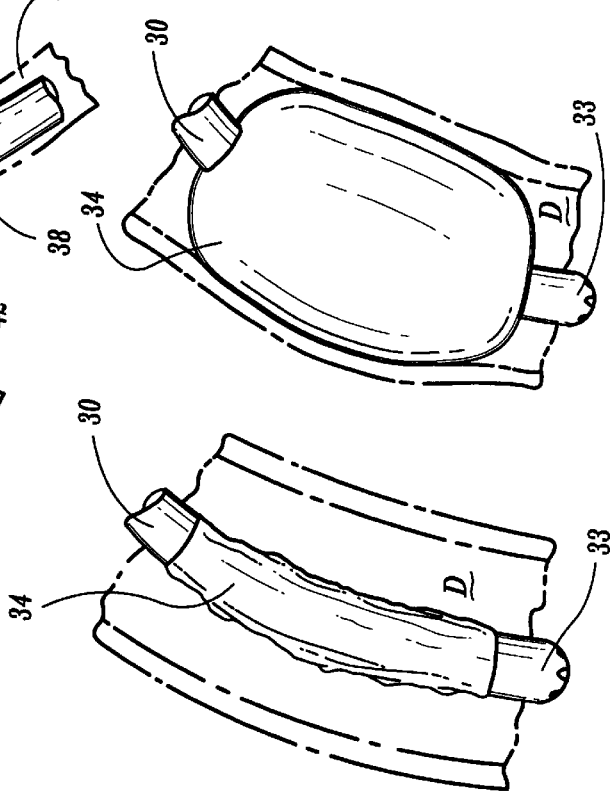

CATHETER SYSTEM

BACKGROUND

1. Field of the Invention

The present application relates to a catheter system, and, more particularly, to a percutaneous catheter system for transporting blood during surgical procedures.

2. Background of the Related Art

During surgical heart procedures such as bypass or valve surgery, blood is withdrawn from the venous side of the patient, transported through a heart lung machine where it is oxygenated, and returned to the patient's arterial side for distribution throughout the body. Thus, the heart is bypassed and the heart lung machine performs the pumping function of the heart. Typically, the blood is withdrawn by a venous catheter inserted into the right atrium or the vena cava and the blood is returned by an arterial catheter inserted into the aorta. The aorta must be clamped to isolate the left atrium and ventricle of the heart to prevent the returned blood from entering therein. Such clamping, however, can cause damage to the internal wall of the aorta as well as cause plaque to be separated from the aorta and enter the patient's bloodstream.

Conventionally, bypass procedures were performed by opening the sternum via a long incision in an invasive procedure, resulting in a lengthy recovery period for the patient. Arterial and venous access for the cannulas connecting to the heart lung machine, as well as cross-clamping the aorta, was achieved through the large opening in the sternum.

With the advent of minimally invasive surgical procedures which enabled heart surgery to be performed through a small window in the patent's chest or through cannulas inserted through small incisions between the ribs, the need existed for a minimally invasive way to achieve arterial and venous catheter access as well as to isolate the left side of the heart European patent application 218,275 describes an arterial catheter for open heart surgery designed to avoid clamping the aorta by providing an inflatable balloon to occlude the blood vessel. The catheter includes a channel for the delivery of cardioplegia fluid into the heart to arrest the heart or for venting fluid from the heart and a separate channel to transport the blood from the bypass machine to the aorta. The application states that the balloon also has the advantage of keeping the tip of the catheter spaced from the vessel wall so the blood vessel tissue cannot obstruct blood flow through the catheter tip. The arterial catheter is described as being inserted into the aorta, near the aortic valve. In an alternate embodiment, the catheter's position in the aorta is reversed.

U.S. Pat. No. 5,312,344 to Grinfeld et al also discloses an arterial perfusion cannula designed to avoid the trauma of aortic clamps. The catheter has one or two balloons to occlude the arterial vessel in the ascending aorta between the aortic valve and the coronary ostium, a pathway for fluid to inflate the balloon, a pathway to transport blood from the bypass machine through the catheter, and a pathway for cardioplegia solution or venting. In one embodiment, the catheter is inserted through the ascending aorta and in an alternate embodiment it is inserted through the femoral artery.

U.S. Pat. No. 5,478,309 to Sweezer et al. also discloses an arterial catheter system having an occlusion balloon, a pathway for cardioplegia or venting, and a passage for blood flow. The occlusion balloon and pathway for cardioplegia are positioned on a second cannula which is slidably mounted within the blood flow cannula. Different methods of insertion of the catheters are described, namely insertion through the subclavian artery, through the femoral artery and directly into the aorta through a trocar port.

Insertion through the femoral artery and subclavian artery does provide a minimally invasive approach as it achieves access without a large opening in the chest cavity, However, since these arteries are small, insertion through these arteries requires a small catheter. Patients undergoing heart surgery have plaque buildup in the arteries which can obstruct insertion of the catheters. The plaque buildup further reduces the internal diameter of the artery. Also, the catheters, if too large, can scrape off the plaque and send it into the bloodstream, causing a stroke. Consequently, the foregoing affect the maximum feasible diameter of the catheter.

On the other hand, the minimum feasible diameter of the catheter is dictated by the fact that the catheter must have three separate pathways: for cardioplegia (and venting), balloon inflation and blood flow. The blood flow passage size is critical since it must be sufficient to return the blood to the patient undamaged.

Sweezer '309, in an attempt to limit the size of the catheter, describes a complex telescoping cannula arrangement. The catheter is of relatively large size since it must have an opening for blood flow, cardioplegia, balloon inflation and as well as a passageway to receive another cannula. Moreover, in Sweezer's femoral access approach, the blood is returned in a retrograde fashion, i.e. opposite the normal direction of blood flow, in a region of the body far removed from the aortic arch and the major vessels feeding the upper body. Thus, there is the risk that sufficient blood cannot be supplied to the upper regions of the body, e.g. the brain.

The need therefore exists for an arterial occlusion catheter system which has a large enough passage to return the blood, undamaged, to the patient's arterial side but is small enough to be inserted minimally invasively without the aforementioned adverse affects on the patient.

SUMMARY OF THE INVENTION

The present application provides an arterial cannula system for transporting blood from an extracorporeal pump to a patient's femoral artery and aorta comprising first and second cannula portions. The first cannula portion has a proximal portion, a distal portion, and an intermediate portion and is configured for insertion through the femoral artery. It includes a first lumen having an opening in the distal portion to deliver cardioplegic fluid, a second lumen communicating with an expandable occluding member at the distal end portion to inflate the occluding member to occlude blood flow, and a third lumen extending from the proximal portion to the intermediate portion to transport blood from the extracorporeal pump to the femoral artery. The second cannula portion is configured for insertion into the subclavian artery so that an opening in the distal portion is in communication with the aorta. A lumen extending through the second cannula portion is in communication with the opening to transport blood from the extracorporeal pump to the aorta.

In one embodiment, the distal end portion of the second cannula portion has a plurality of openings to provide a plurality of ports for passage of blood to the aorta. The intermediate portion of the first cannula portion may also include a plurality of openings to provide a plurality of ports for the passage of blood to the femoral artery or lower body. The first and second cannula portions may each have a first diameter at the proximal end portion greater than a second diameter at the distal portion.

In an alternate embodiment, the distalmost tip of the first cannula portion does not protrude distally of the expandable occluding member.

The present application may also provide a catheter comprising a proximal portion adapted to be connected to an extracorporeal pump to transport blood from the pump and a bifurcated portion distal of the proximal portion defining first and second cannulas. The first cannula has at least one opening to supply blood to a lower region of the body, e.g. the femoral artery, and further has an occluding member to block the flow of blood to a second region of the body, e.g. the left ventricle. The second cannula has at least one opening to supply blood to an upper region of the body, e.g. the aorta. The at least one opening in the first and second cannulas are in fluid communication with a passageway in the proximal portion of the catheter.

The catheter systems disclosed herein may further include a venous catheter adapted to be connected to the extracorporeal pump to transport blood from the patient's body to the pump and is preferably configured for insertion through the femoral vein.

The present application also provides a method for supplying blood to a patient from an extracorporeal blood pump comprising the steps of inserting a first cannula percutaneously through the femoral artery of the patient, transporting blood from an extracorporeal pump through a first lumen in the first cannula to supply blood to the femoral artery, supplying cardioplegic fluid to the left ventricle through a second lumen in the first cannula, inserting a second cannula percutaneously through the brachial and subclavian artery of the patient, and transporting blood through a first lumen in the second cannula to supply blood to the aorta. The method preferably further includes the step of providing an occluding member on the distal portion of the first cannula to stop blood flow to the left ventricle.

The method may further comprise the step of inserting a venous cannula percutaneously through the femoral vein to withdraw blood from the venous side and transport it to the extracorporeal pump.

A method of supplying blood to the femoral artery and the aorta during a surgical procedure is also provided comprising the steps of inserting a first arterial catheter percutaneously at a first location to supply blood to the femoral artery, inflating an inflatable member on the first catheter to occlude blood flow to the heart, and inserting a second arterial catheter percutaneously at a second location to supply blood to the aorta.

BRIEF DESCRIPTION OF THE DRAWINGS

Preferred embodiments of the present disclosure are described herein with reference to the drawings wherein:

FIG. 1D is an enlarged view of the bifurcated portion of the arterial catheter of FIG. 1;

FIG. 2B is an enlarged view illustrating the attachment of the arterial cannulas of FIG. 2A to the Y-connector;

FIG. 3 is an enlarged view of the distal end of the subclavian arterial cannula of FIG. 1;

FIG. 3A is an enlarged view of the distal end of an alternate embodiment of the subclavian arterial cannula having a plurality of blood flow openings;

FIG. 4 is an enlarged view of the distal end of the femoral arterial cannula of FIG. 1;

FIG. 4A is an enlarged view of the distal end of an alternate embodiment of the femoral arterial cannula having a plurality of blood flow openings;

FIGS. 5 and 5A are enlarged views of the distal tip of the femoral arterial cannula of FIG. 1 showing the balloon in a deflated and inflated position, respectively;

FIGS. 5B and 5C are enlarged views of the distal tip of another alternate embodiment of the femoral arterial cannula showing the balloon in a deflated and inflated position, respectively;

DETAILED DESCRIPTION OF PREFERRED EMBODIMENTS

Figure 1:
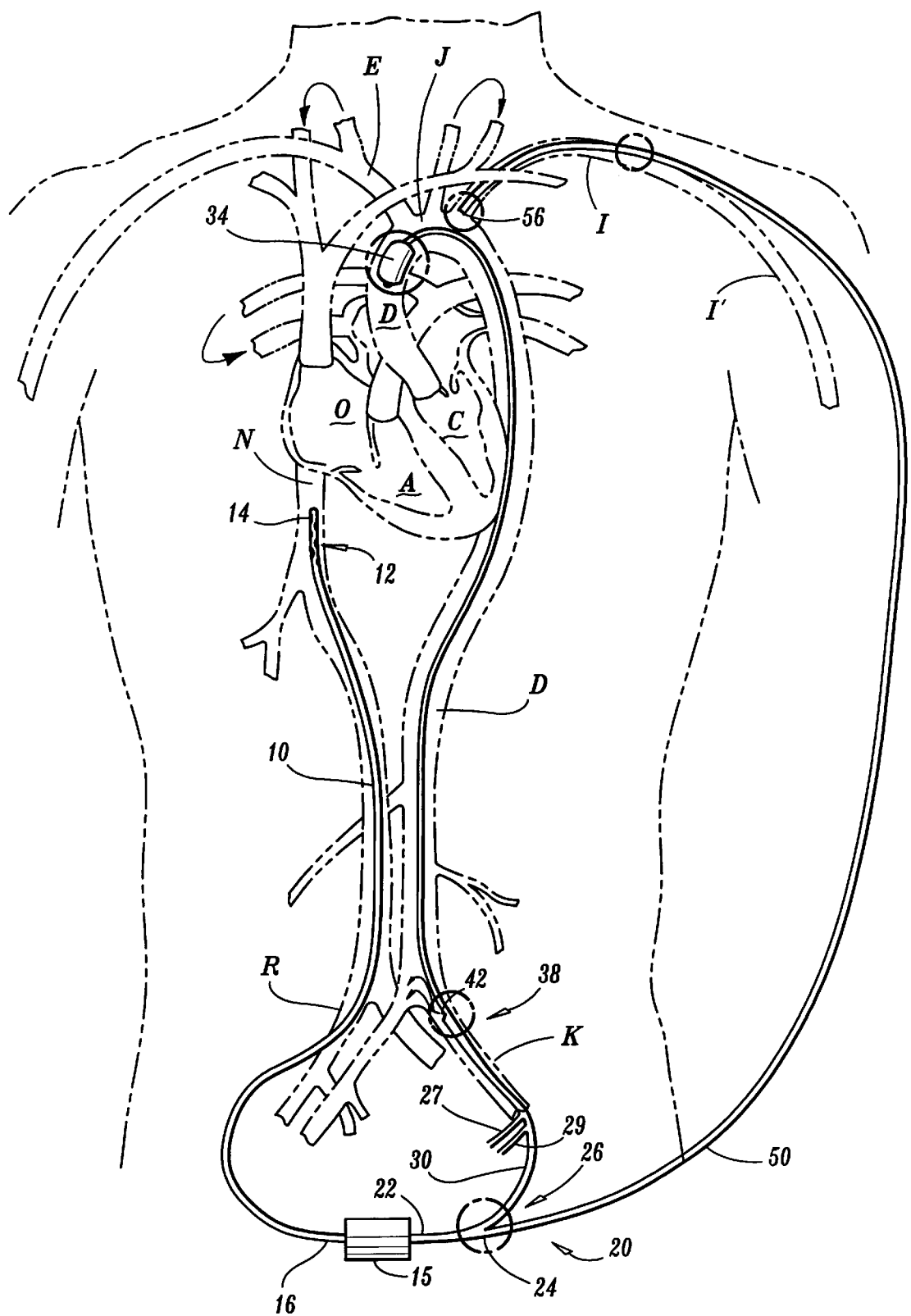
FIG. 1 is a view illustrating a venous and arterial catheter system in accordance with a first embodiment of the present disclosure wherein the venous catheter is inserted through the femoral vein into the vena cava, one arterial catheter (cannula) is inserted through the left femoral artery and the other arterial catheter (cannula) is inserted through the left subclavian artery.

Preferred embodiments of the presently disclosed catheter system will now be described in detail with reference to the drawings in which like reference numerals designate identical or corresponding elements in each of the several views. As discussed herein, the term proximal refers to the area further from the patient and the term distal refers to the area closer to the patient At the outset, to facilitate understanding of the present disclosure, a brief description of blood flow through the heart is provided. In short, with reference to FIG. 1A, blood flows from the right ventricle A through the pulmonary arteries where it is oxygenated by the lungs. Blood flow continues through the pulmonary veins, into the left atrium B and left ventricle C where it is then pumped into the aorta D and the three major arteries branching from the arch of the aorta which supply blood to the upper part of the body: the brachiocephalic trunk E (innominate artery) which divides into the right subclavian artery F and the right carotid artery G; the left carotid artery H; and the left subclavian artery I. Blood flow continues around the arch J of the aorta and through the aorta D where it divides into the left and right femoral arteries K, L in the left and right legs, respectively. The femoral arteries and the lower regions of the aorta feed the lower regions of the body. The superior vena cava M and the inferior vena cava N transport the blood from the upper and lower regions of the body into the right atrium O and right ventricle A.

During conventional bypass or heart valve surgery, the patient's blood is diverted from the heart and transported to a heart-lung (or cardiopulmonary bypass) machine where the blood is oxygenated and then returned to the body. In use of the conventional heart lung machine, one cannula is inserted on the venous side (e.g. vena cava) of the patient's body, referred to as a venous catheter, to withdraw blood from the body before it reaches the right atrium. Another cannula is inserted into the aorta to return the oxygenated blood from the bypass machine to the body, referred to as an arterial catheter. The aorta is clamped so that blood flow into the left atrium and left ventricle is prevented.

The catheter system of the present disclosure which provides both venous and arterial catheter access minimally invasively will now be described. That is, the venous and arterial catheters are inserted percutaneously through a small incision to provide less traumatic connection to a heart-lung machine or other extracorporeal pump.

Figure 1A:
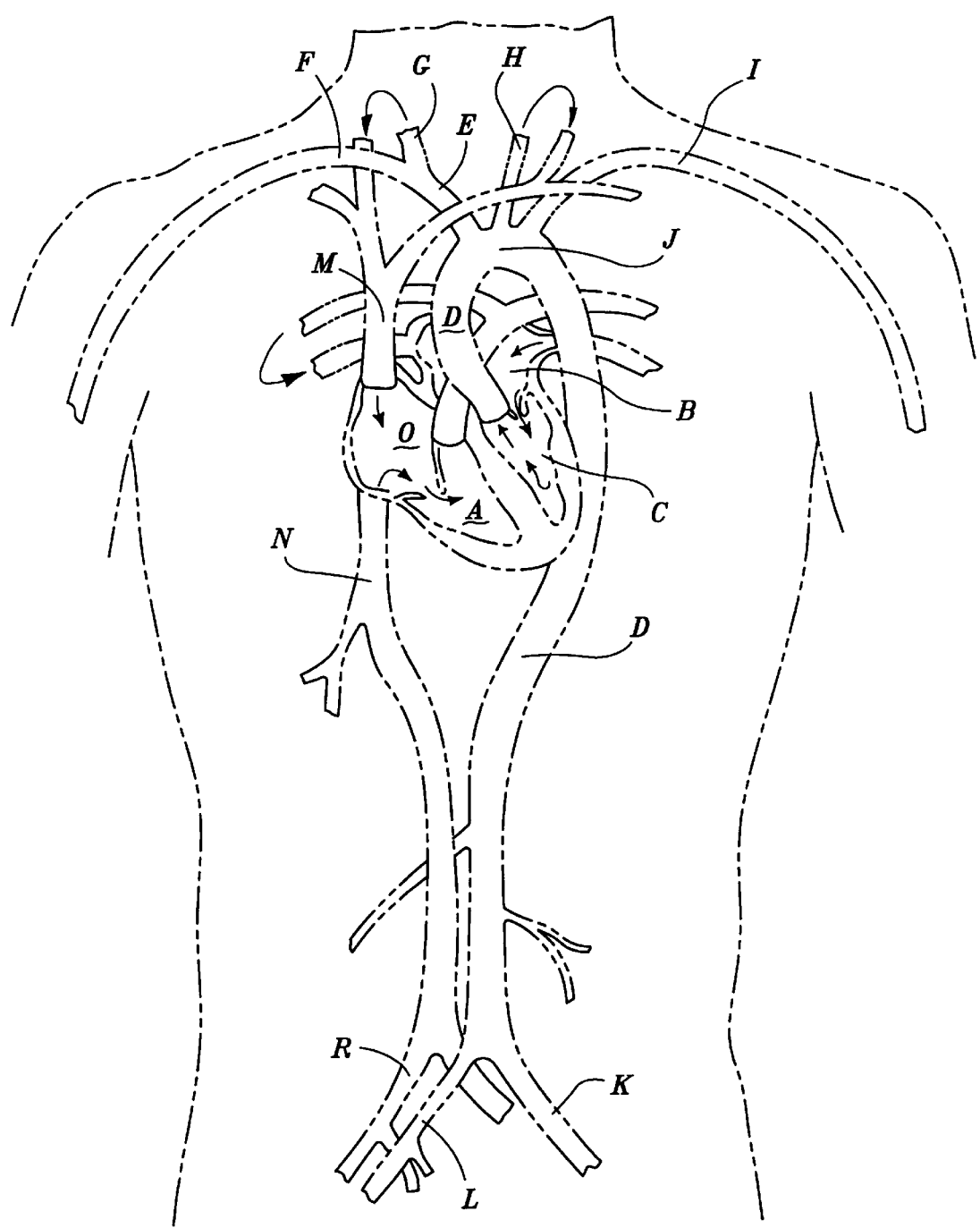
FIG. 1A is a view illustrating generally the blood flow to and from the heart.

As shown in FIG. 1, a venous cannula (catheter) 10 is inserted through the femoral vein R so that it's distal end 12 with openings 14 communicates with the inferior vena cava N to withdraw blood from the body before it enters into the right atrium 0. The proximal end 16 of the venous cannula 10 is connected to a conventional bypass machine 15, represented schematically. Thus blood is transported through openings 14, through a passageway extending the length of cannula 10, and out the proximal end 16 into the bypass machine. It is also contemplated that other extracorporeal pumps can be utilized with the catheter system disclosed herein, provided these pumps include either an oxygenator as an integral component or an in-line oxygenator for oxygenating the blood before it is returned to the body through the arterial catheter system. One such system is illustrated schematically in FIG. 7, with reference letter Y designating the pump and reference letter Z designating the oxygenator.

Figure 1B:
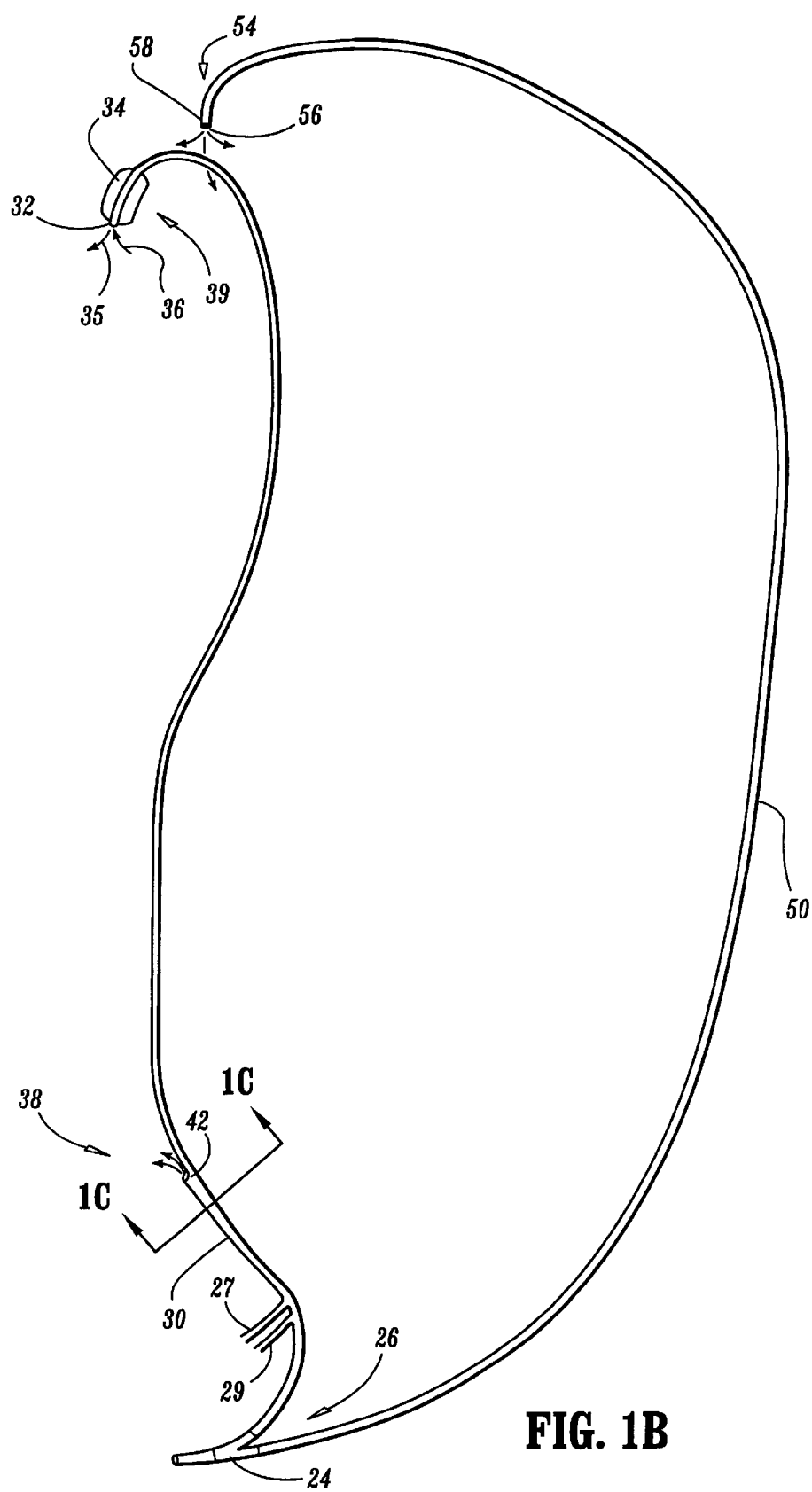
FIG. 1B is a view illustrating the arterial catheter system of FIG. 1.

Turning now to the first embodiment of the arterial catheter system and with reference to FIGS. 1 and 1B, arterial catheter 20 has a first cannula or catheter 30 configured and dimensioned for insertion through the left femoral artery K and a second cannula or catheter 50 configured and dimensioned for insertion through the left brachial artery I' and the left subclavian artery I. Catheter 20 is connected at the proximal end portion 22 to the heart lung machine 15 to transport blood from the machine to the patient's body. Catheter 20 is bifurcated at region 24 to define the first and second cannulas 30 and 50 (see also FIG. 1D).

First cannula 30, which can be referred to as the femoral access cannula, is inserted percutaneously through the left femoral artery K and snaked through the aorta D around the arch J so that the distal tip 32 is beyond the brachiocephalic trunk E. Femoral access cannula 20 generally includes a proximal portion 26, an intermediate portion 38 and a distal portion 39. Distal portion 39 includes an occluding member 34, preferably an expandable balloon, which can be inflated to prevent blood flow to the left ventricle C. A lumen 33 communicates with the balloon 34 and extends through the cannula 30 to communicate with tube 27 which connects to a saline source for inflation. A series of openings (not shown) at the distal tip 32 are in communication with a second lumen 31 which also extends through the cannula 30 to communicate with tube 29 to supply cardioplegia fluid to the left ventricle C, represented by arrow 35, to arrest the heart as is conventional during the surgical procedure. The openings for cardioplegia can also be used for venting the left ventricle C prior to or during the procedure, represented by arrow 36.

The intermediate portion 38 of the femoral access cannula 30 has an opening 42 as shown to provide a port for returning blood to the body. As illustrated, the opening 42 is in communication with the femoral artery K (see also FIG. 4). A third lumen 44 extends from the bypass machine through the proximal portion and to opening 42 so that blood can be transported from the bypass machine to the femoral artery K to supply blood to the lower regions of the body.

In a preferred embodiment, the outer diameter of the femoral access cannula 30 up to the intermediate portion 38 where the blood exits through opening 42 ranges from about 0.26 to about 0.31 inches in diameter and more preferably is about 0.27 inches in diameter. The section of the cannula distal of the blood exit opening 42 is preferably smaller and preferably has an outer diameter ranging from about 0.131 inches (10F) to about 0.158 inches (12F) and more preferably about 0.144 inches (11F). Other dimensions are contemplated. Thus, it can be appreciated that the portion of the cannula which needs to be snaked up through the aorta and around the aortic arch can be made smaller since it does not require an additional large lumen for blood flow. Consequently, unobstructed insertion of the cannula is facilitated.

Turning now to the second cannula (catheter), designated by reference numeral 50 and which can be referred to herein as the subclavian access cannula, this cannula is also illustrated in FIGS. 1 and 1B. The subclavian cannula 50 forms the second leg of the bifurcation and is percutaneously inserted through the left brachial artery I' in the arm/shoulder region, through the subclavian artery I and into arch J of the aorta D. A central lumen (not shown) extends from the bifurcation (communicating with lumen 44) through the length of the cannula, terminating at the distal end portion 54. An opening 56 is formed at the distal tip 58 to provide a port for the return of blood from the central lumen to the aorta D (see also FIG. 3), thereby feeding the upper regions of the body as the returned blood flows through the major arteries as described above.

The subclavian access catheter 50 preferably has an outer diameter ranging from about 0.170 inches (13F) to about 0.197 inches (15F), and preferably about 0.184 inches (14F).

Figures 1C, 2A:
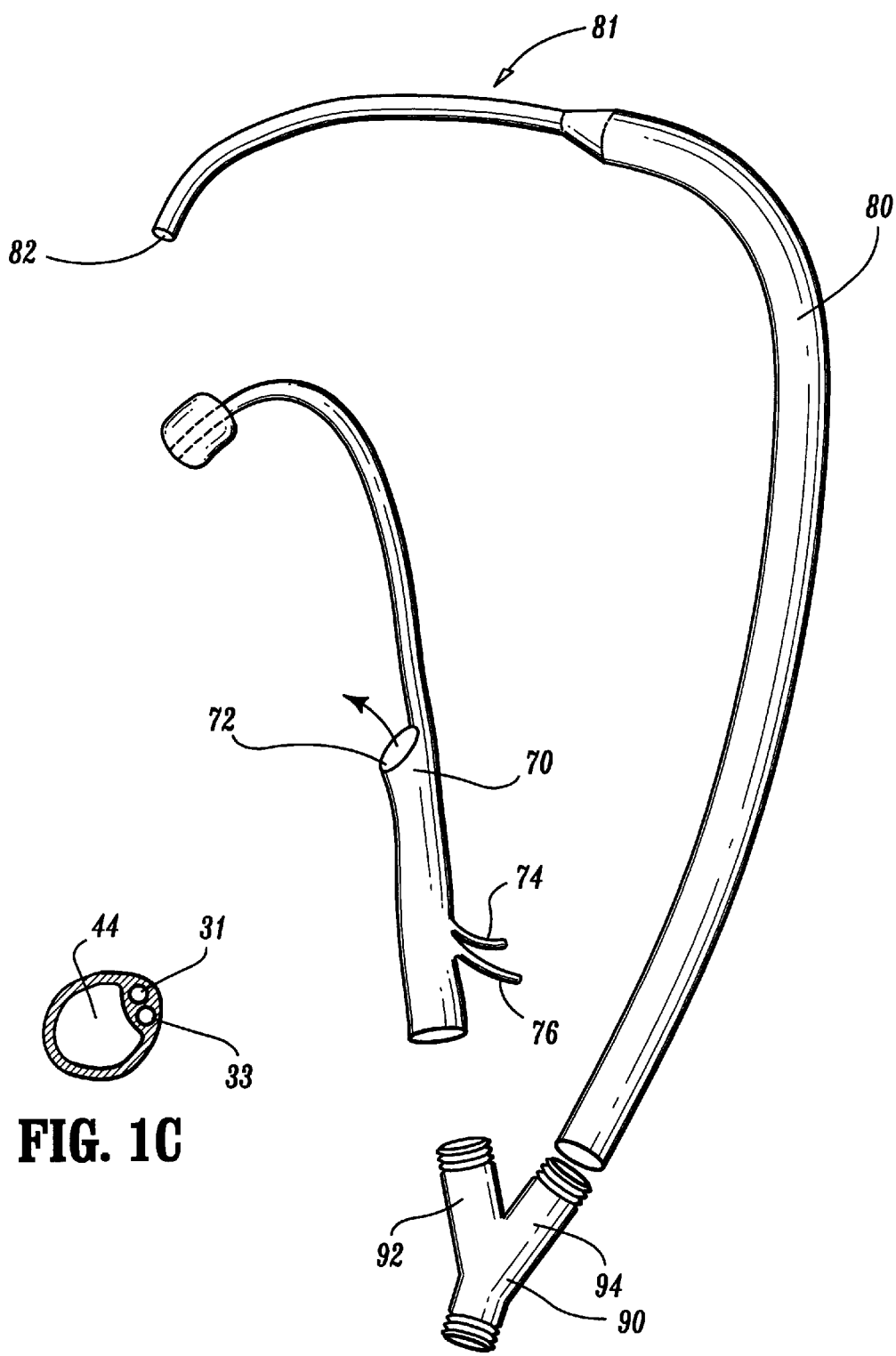
FIG. 1C is a cross sectional view taken along lines 1C—1C of FIG. 1B.
FIG. 2A is a viewing illustrating an alternate embodiment of the arterial catheter system.

It is also contemplated that the subclavian access catheter 50 can have a reduced diameter at the portion which is inserted into the body to facilitate access to the aorta. This is illustrated in FIG. 2A. The reduced diameter section preferably has an outer diameter of about 0.170 inches (13F) to about 0.197 inches (15F) and more preferably about 0.184 inches (14F).

Other dimensions for the subclavian catheter are also contemplated.

In use, with reference to FIG. 1 the venous catheter 10 is inserted percutaneously through the femoral vein R so that the blood receiving openings 14 are in communication with the inferior vena cava N. The arterial catheter 20 is inserted so that one portion of the catheter, e.g. first cannula 30, is inserted percutaneously through the left femoral artery K and up through the aorta D around the arch J of the aorta. The balloon 34 at the distal end is inflated via lumen 33 to occlude blood flow to the left ventricle C. If desired, the left ventricle can be vented through the distal openings as described above. Cardioplegia fluid is injected through second lumen 31 into the left ventricle C to arrest the heart. The second portion of the arterial catheter 20, e.g. second cannula 50, is inserted percutaneously through the left brachial artery I', through the left subclavian artery I and into the arch J of the aorta so that the opening 56 at distal tip 58 is in communication with the aorta D. Therefore, as can be appreciated, blood withdrawn from the inferior vena cava N travels through the passageway of venous catheter 10 through the bypass machine 15, and through the lumen 44 of proximal end portion 22 of arterial catheter 20. Distal (downstream) of the connection to the bypass machine 15, the blood is divided at bifurcation 24 so that one portion flows through lumen 44 of femoral access cannula 30 and exits opening 42 into the femoral artery K to feed the lower regions of the body and the other portion of the blood flows through the central lumen of the subclavian access cannula 50 to exit opening 56 to supply blood to the aorta D for feeding the upper regions of the body.

An alternate embodiment of the subclavian access cannula is illustrated in FIG. 3A. As shown, instead of a single opening for blood flow as in the embodiment of FIG. 1, a plurality of openings 60 are provided in the side wall of the cannula 50' to provide of a series of exit ports for blood flow. Similarly, an alternate embodiment of the femoral access cannula is illustrated in FIG. 4A wherein a plurality of openings 66 are provided in the side wall of cannula 30' to provide several ports for blood flow.

An alternate embodiment of the arterial catheter system is illustrated in FIG. 2A. Instead of a single catheter which is bifurcated into two catheter sections, two separate catheters (cannulas) are provided which are attached to a Y connector 90 as shown in FIG. 2. Y-Connector 90 includes a first leg 92 for mounting the femoral access catheter 70 and a second leg 94 for mounting the subclavian access catheter 80. Leg 92 includes a lumen (not shown) communicating with the blood flow lumen of catheter 80 to transport blood out through opening 72. Tubes 74 and 76 are for cardioplegia and balloon inflation as in the embodiment of FIG. 1. Leg 94 contains a single lumen communicating with the central lumen of subclavian arterial catheter 80 to enable blood flow therethrough to exit distal opening 82. Subclavian access catheter 80 is shown with a reduced diameter portion 81 as described above, but can also be configured with a uniform diameter as in the embodiment of FIG. 1.

The catheters 70 and 80 can be threaded onto, snap fitted or attached by any other means to the Y connector as long as blood flow is unimpeded from the bypass machine, through the connection cannula 75 (FIG, 2), and through the lumen of Y connector 90 where it is divided for flow into the lumens of the femoral and subclavian access catheters 70, 80. It should also be appreciated that instead of a Y connector separate from the bypass machine, it is contemplated that the femoral and subclavian access catheters can be separately attached to the bypass machine.

Figure 6:
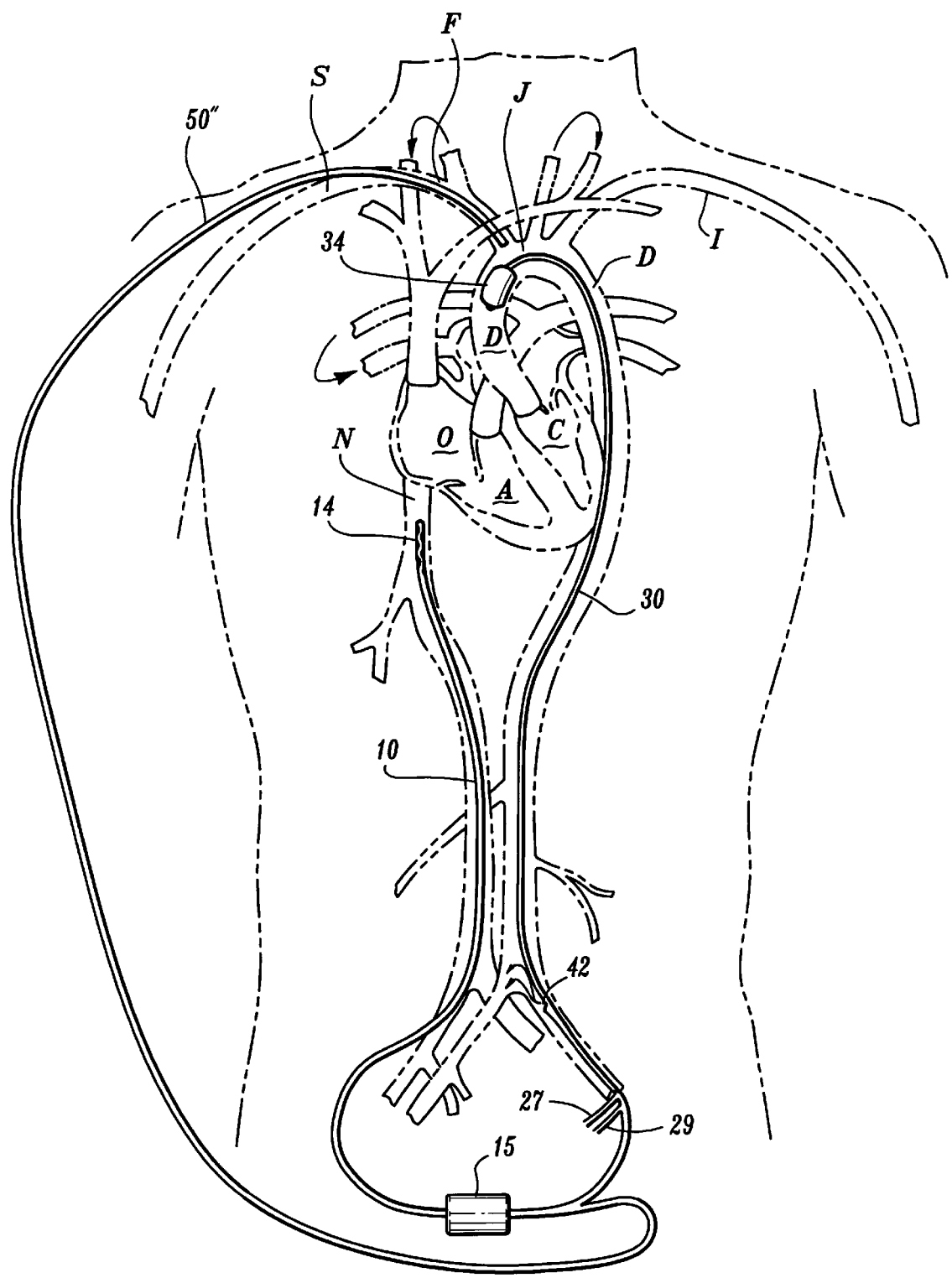
FIG. 6 is a view of an alternate method of catheter insertion illustrating the venous catheter inserted into the vena cava, one arterial catheter inserted through the left femoral artery and the other arterial catheter inserted through the right subclavian artery.

FIG. 6 illustrates an alternate method of insertion of the arterial catheter system of the present disclosure. The catheter configurations are identical to that of FIG. 1 and the method of insertion differs from FIG. 1 only in that the subclavian access catheter 50" is inserted through the right side instead of the left side of the body. That is, cannula 50" is inserted through the right brachial artery S and the right subclavian artery F and into the arch J of the aorta D as shown. In all other respects, the catheter system operates in the same way as the above described catheter system of FIG. 1.

Figure 7:
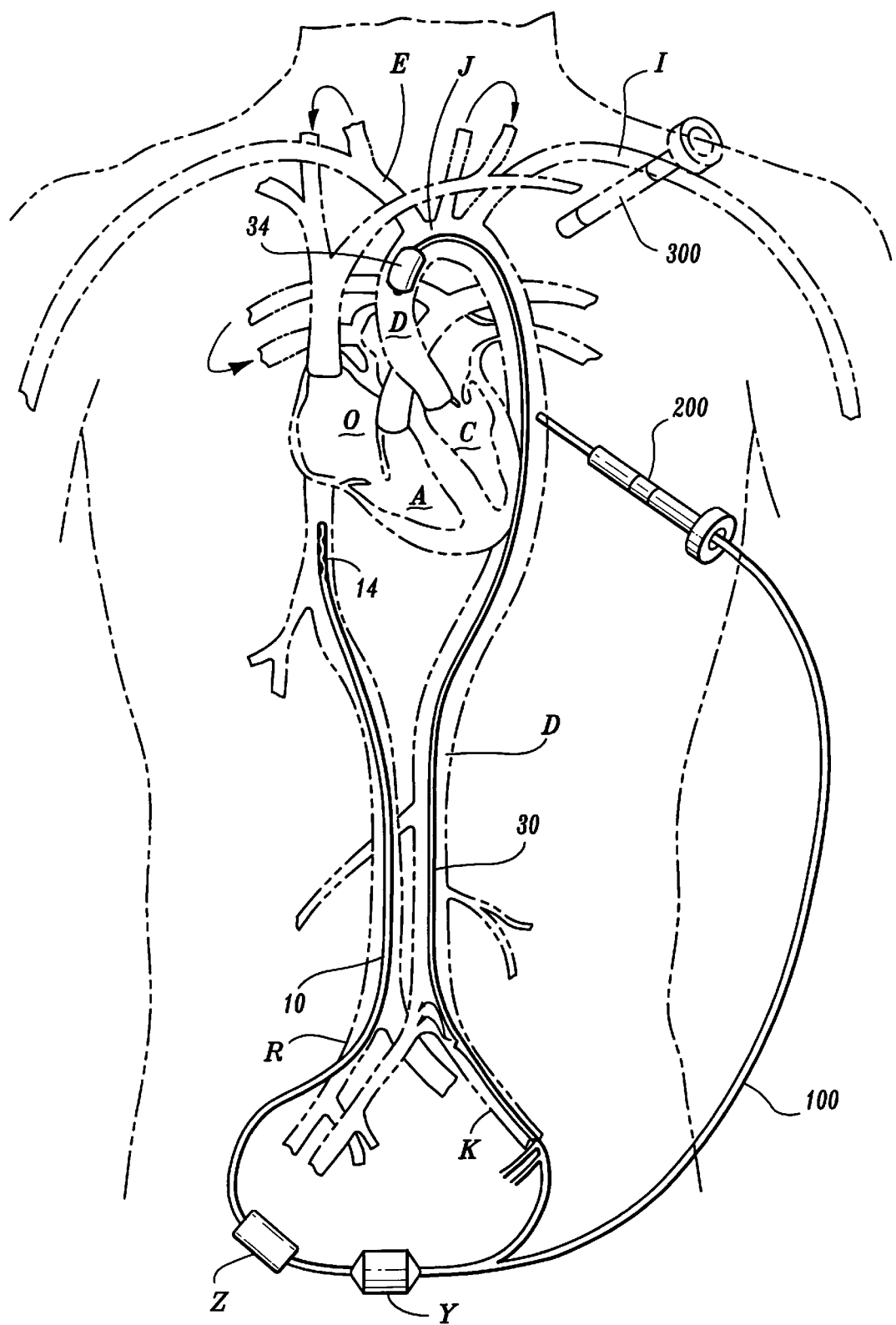
FIG. 7 is a view of another alternate method of catheter insertion illustrating the venous catheter inserted into the vena cava, one arterial cannula inserted through the left femoral artery and the other arterial cannula inserted thoracopically through a trocar.

FIG. 7 depicts another alternate method of insertion of the subclavian access catheter. In this method, the femoral access cannula 30 and venous cannula 10 are identical and inserted in an identical manner as in FIG. 1. However, the second arterial cannula 100 is inserted thoracoscopically through a conventional trocar 200 instead of percutaneously through the brachial artery. As shown, trocar 200 is positioned between the patient's ribs to provide access to the aorta. The trocar 200 can have a penetrating tip to penetrate directly into the aorta to enable the insertion of the cannula directly into the aorta or alternatively the cannula can have a penetrating tip. It should be appreciated that the trocar can be inserted at other locations as well. By way of example, one alternate location for trocar insertion is depicted in phantom and designated by reference numeral 300 in FIG. 7.

In the above described embodiments, the distalmost tip 52 of the femoral access catheter 30 is positioned distal of the balloon. Consequently, it is possible that this tip could contact the vessel walls as the cannula is inserted before the balloon is inflated. FIGS. 5B and 5C illustrate an alternate embodiment where the distalmost tip 33" of the catheter 30" is recessed with respect to the balloon 34". This eliminates the risk of unwanted contact between the vessel wall and the catheter. As shown, the tip 33" remains proximal of the balloon when the balloon is both deflated and inflated. It should be appreciated that this balloon/distal tip arrangement where the tip is flush or recessed with respect to the balloon can be utilized with catheters other tan those described in the present application.

It will be understood that various modifications may be made to the embodiments herein therefore, the above description should not be construed as limiting but merely as exemplifications of preferred embodiments. For example, in any of the aforedescribed methods of insertion, the femoral access catheter can be inserted through the right femoral artery instead of the left femoral artery. Those skilled in the art will envision other modifications within the scope and spirit of the claims appended hereto.

What is claimed:

1. An arterial cannula system for transporting blood to a patient's femoral artery and aorta, the cannula system comprising:

an extracorporeal pump having a blood flow inlet and a blood outflow outlet;

a first arterial cannula portion having a proximal portion, a distal portion, an intermediate portion between the proximal and distal portions, a first lumen having an opening in the distal portion to deliver cardioplegic fluid, an expandable occluding member disposed at the distal portion, a second lumen communicating with the expandable member to inflate the expandable member to occlude blood flow, and a third lumen in fluid communication with the outlet of the extracorporeal pump and positioned and arranged to receive blood pumped thereby, and extending from the proximal portion to the intermediate portion of the first cannula portion and terminating proximal of the occluding member for passage of blood from the extracorporeal pump to the femoral artery, the first cannula portion configured for insertion through the femoral artery; and a second arterial cannula portion having a distal portion and an opening in the distal portion, the second cannula portion configured for insertion into the subclavian artery so the opening in the distal portion is in communication with the aorta, and a lumen in fluid communication with, and receiving, the outlet of the extracorporeal pump and extending through the second cannula portion in communication with the opening for passage of blood from the extracorporeal pump to the aorta.

2. An arterial cannula system according to claim 1, further comprising a plurality of openings in the distal portion of the second cannula portion to provide a plurality of ports for passage of blood to the aorta.

3. An arterial cannula system according to claim 2, wherein the distal tip of the first cannula portion is configured for insertion adjacent the left ventricle to enable venting of the ventricle through the first lumen.

4. An arterial cannula system according to claim 1, wherein the first cannula portion has an outer diameter ranging from about 0.1 inches to about 0.4 inches.

5. An arterial cannula system according to claim 1, wherein the second cannula portion has an outer diameter ranging from about 0.1 inches to about 0.4 inches.

6. An arterial cannula system for transporting blood from an extracorporeal pump to a patient's femoral artery and aorta, the cannula system comprising:

a first arterial cannula portion having a proximal portion, a distal portion, an intermediate portion between the proximal and distal portions, a first lumen having an opening in the distal portion to deliver cardioplegic fluid, an expandable occluding member disposed at the distal portion, a second lumen communicating with the expandable member to inflate the expandable member to occlude blood flow, and a third lumen extending from the proximal portion to the intermediate portion for passage of blood from the extracorporeal pump to the femoral artery, the third lumen terminating proximal of the occluding member; the first cannula portion configured for insertion through the femoral artery;

a second arterial cannula portion having a distal portion and an opening in the distal portion, the second cannula portion configured for insertion into the subclavian artery so the opening in the distal portion is in communication with the aorta, and a lumen extending through the second cannula portion in communication with the opening for passage of blood from the extracorporeal pump to the aorta, the opening being adjacent the distal end portion of the first cannula portion; and a Y connector having first and second legs for mounting the first and second cannula portions, respectively.

7. An arterial cannula system according to claim 6, further comprising a tube connecting the Y connector to the extracorporeal pump.

8. An arterial cannula system according to claim 1, wherein the first cannula portion has a first diameter at the proximal portion and a second diameter at the distal portion, the first diameter being greater than the second diameter.

9. An arterial cannula system according to claim 1, wherein the second cannula portion has a reduced outer diameter section.

10. An arterial cannula system according to claim 1, wherein a distalmost tip of the first cannula portion does not extend distally of the expandable member.

11. An arterial cannula system according to claim 1, further comprising a plurality of openings in the intermediate portion of the first cannula portion to provide a plurality of ports for the passage of blood to the femoral artery.

12. An arterial cannula system according to claim 11, further comprising a plurality of openings in the distal portion of the second cannula portion to provide a plurality of ports for the passage of blood to the aorta.

13. A catheter system comprising:

an arterial catheter having a proximal portion adapted to be connected to an extracorporeal pump and a bifurcated portion distal of the proximal portion and defining a first catheter dimensioned for insertion through a femoral artery and having at least one blood flow opening to supply blood to the femoral artery and a second catheter dimensioned for insertion through a brachial artery and subclavian artery to supply blood to the aorta, the first catheter including an occluding member at a distal portion to block blood flow to the left ventricle and at least one opening to supply cardioplegic fluid to the left ventricle, the occluding member and the at least one cardioplegic fluid opening positioned distal of the at least one blood flow opening.

14. A catheter system according to claim 13, wherein the first catheter has a first port spaced from the distal portion and in fluid communication with the extracorporeal pump to supply blood to the femoral artery.

15. A catheter system according to claim 14, wherein the distalmost tip of the first catheter does not protrude beyond the occluding member.

16. A catheter system according to claim 13, wherein the occluding member is an inflatable balloon and the first catheter includes a lumen communicating with the balloon for the passage of fluid to inflate the balloon.

17. A catheter system according to claim 13, further comprising a venous catheter adapted to be connected to the extracorporeal pump to transport blood from the patient's body to the pump.

18. A catheter system according to claim 17, wherein the venous catheter is configured for insertion through the femoral vein.

19. A catheter system according to claim 18, further comprising at oxygenator interposed between the venous catheter and the arterial catheter.

20. A catheter comprising:

a proximal portion adapted to be connected to an extracorporeal pump to transport blood from the pump and a bifurcated portion distal of the proximal portion and defining first and second cannulas, the first cannula having at least one opening to supply blood to a lower region of the body and further having an occluding member to block the flow of blood to a second region of the body, the occluding member positioned distal of the at least one opening, the second cannula having at least one opening to supply blood to an upper region of the body, the at least one opening in the first and second cannulas being in fluid communication with a passageway in the proximal portion of the catheter.

21. An arterial cannula system for transporting blood from an extracorporeal pump to a patient's arterial system which comprises:

an elongated cannula adapted to be connected to an extracorporeal pump and defining at least one blood flow lumen to transport blood from the extracorporeal pump, the elongated cannula including:

a first cannula portion configured for insertion through the femoral artery and having proximal and distal ends, the first cannula portion having an expandable occluding member disposed adjacent the distal end, a first lumen to inflate the expandable member and a second lumen defining a blood flow lumen to transport blood from the extracorporeal pump;

a second cannula portion configured for insertion into the subclavian artery, the second cannula portion including a lumen defining a blood flow lumen to transport blood from the extracorporeal pump; and a pump connecting portion connectable to the extracorporeal pump, the pump connecting portion defining a lumen in fluid communication with an output of the extracorporeal pump for passage of blood, the lumen of the pump connecting portion being in fluid communication with the blood flow lumen of the first cannula portion and in fluid communication with the blood flow lumen of the second cannula portion to direct the blood to the respective blood flow lumens of the first and second cannula portions.

22. An arterial cannula system for transporting blood to a patient's arterial system, which comprises:

an extracorporeal pump having a blood flow inlet and a blood flow outlet;

a first cannula portion configured for insertion through a femoral artery and having proximal and distal ends, the first cannula portion having an occluding member adjacent the distal end dimensioned to occlude the femoral artery and a first lumen in communication with the occluding member to expand the expandable member to occlude blood flow, a second lumen in fluid communication with the blood outflow outlet of the extracorporeal pump for passage of blood from the extracorporeal pump and terminating in a blood opening disposed proximal of the occluding member to permit blood to enter the femoral artery;

a second cannula portion configured for insertion into the subclavian artery and having proximal and distal ends, the second cannula portion having a lumen in fluid communication with the blood outflow outlet of the extracorporeal pump for passage of blood from the extracorporeal pump and terminating in a blood opening adjacent the distal end to permit blood to enter the subclavian artery; and a pump connecting portion connectable to the extracorporeal pump, the pump connecting portion defining a lumen in fluid communication with the blood flow outlet of the extracorporeal pump for passage of blood, the lumen of the pump connecting portion being in fluid communication with the second lumen of the first cannula portion and in fluid communication with the lumen of the second cannula portion to direct the blood to the respective lumens of the first and second cannula portions.

23. An arterial cannula system for transporting blood from an extracorporeal pump to a patient's arterial system which comprises:

an elongated cannula adapted to be connected to an extracorporeal pump and defining at least one blood flow lumen to transport blood from the extracorporeal pump, the elongated cannula including:

a first cannula portion configured for insertion through the femoral artery and having proximal and distal ends, the first cannula portion having an expandable occluding member disposed adjacent the distal end, a first lumen to inflate the expandable member and a second lumen defining a blood flow lumen to transport blood from the extracorporeal pump;

a second cannula portion configured for insertion into the subclavian artery, the second cannula portion including a lumen defining a blood flow lumen to transport blood from the extracorporeal pump;

a pump connecting portion connectable to the extracorporeal pump, the pump connecting portion defining a lumen in fluid communication with an output of the extracorporeal pump for passage of blood, the lumen of the pump connecting portion being in fluid communication with the second lumen of the first cannula portion and in fluid communication with the lumen of the second cannula portion; and a bifurcated portion connecting the first and second cannula portions to the pump connecting portion.

24. An arterial cannula system according to claim 23 wherein the elongated cannula is a monolithically formed device.

25. An arterial cannula system for transporting blood from an extracorporeal pump to a patient's arterial system which comprises:

an elongated cannula adapted to be connected to an extracorporeal pump and defining at least one blood flow lumen to transport blood from the extracorporeal pump, the elongated cannula including:

a first cannula portion configured for insertion through the femoral artery and having proximal and distal ends, the first cannula portion having an expandable occluding member disposed adjacent the distal end, a first lumen to inflate the expandable member and a second lumen defining a blood flow lumen to transport blood from the extracorporeal pump;

a second cannula portion configured for insertion into the subclavian artery, the second cannula portion including a lumen defining a blood flow lumen to transport blood from the extracorporeal pump;

a pump connecting portion connectable to the extracorporeal pump, the pump connecting portion defining a lumen in fluid communication with an output of the extracorporeal pump for passage of blood, the lumen of the pump connecting portion being in fluid communication with the second lumen of the first cannula portion and in fluid communication with the lumen of the second cannula portion; and a Y-connector connecting the first and second cannula portions to the pump connecting portion.

26. An arterial cannula system according to claim 25 wherein the Y-connector and the pump connecting portion are separate devices.

27. An arterial cannula system according to claim 22 further including a bifurcated portion, the bifurcated portion connecting the first and second cannula portions to the pump connecting portion.

28. An arterial cannula system according to claim 27 wherein the pump connecting portion, the bifurcated portion, the first cannula portion and the second cannula portion are a single monolithically formed unit.

29. An arterial cannula system according to claim 22 including a Y-connector, the Y-connector connecting the first and second cannula portions to the pump connecting portion.

* * * * *